United States Patent
Okuhara et al.

(10) Patent No.: US 6,306,950 B1
(45) Date of Patent: *Oct. 23, 2001

(54) CHLORINATED VINYL CHLORIDE RESIN COMPOSITION

(75) Inventors: Toshio Okuhara; Takeyuki Suzuki, both of Hyogo; Minoru Isshiki, Shiga, all of (JP)

(73) Assignee: Kaneka Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/204,082

(22) Filed: Dec. 3, 1998

(30) Foreign Application Priority Data

Dec. 3, 1997 (JP) .................................................. 9-332894

(51) Int. Cl.⁷ ........................................................ C08J 3/22
(52) U.S. Cl. ........................................... 524/497; 524/567
(58) Field of Search ...................................... 524/497, 567

(56) References Cited

U.S. PATENT DOCUMENTS 5,274,043  12/1993  Greenlee et al. ..................... 525/239

FOREIGN PATENT DOCUMENTS

| 2176650 | 11/1996 | (CA) . |
|---|---|---|
| 510 310 | 10/1992 | (EP) . |
| 603 753 | 6/1994 | (EP) . |
| 743 339 | 11/1996 | (EP) . |
| 05-140404 | 6/1993 | (JP) . |
| 05-222261 | 8/1993 | (JP) . |
| 06-157856 | 6/1994 | (JP) . |
| 07-011085 | 1/1995 | (JP) . |

*Primary Examiner*—Peter D. Mulcahy
(74) *Attorney, Agent, or Firm*—Foley & Lardner

(57) ABSTRACT

A chlorinated vinyl chloride resin composition containing a chlorinated vinyl chloride resin which has a polymerization degree of from 600 to 1500 prior to chlorination arid a chlorination degree of from 62 to 70 wt. %, an impact modifier, a stabilizer, a lubricant and titanium dioxide, wherein the content of zinc in titanium dioxide is 0.1% or less, which has improved thermal stability.

6 Claims, No Drawings

CHLORINATED VINYL CHLORIDE RESIN COMPOSITION

BACKGROUND OF THE INVENTION

1. Field of the Invention

The present invention relates to a chlorinated vinyl chloride resin composition. In particular, the present invention relates to a chlorinated vinyl chloride resin composition containing titanium dioxide which improves the thermal stability of the composition.

2. Prior Art

Shaped articles of chlorinated vinyl chloride resin compositions have characteristics such as high heat resistance and are used at relatively high temperatures at which conventional vinyl chloride resin compositions cannot be used due to thermal deformation. For example, the shaped articles of chlorinated vinyl chloride resin compositions are used in the form of a pipe for hot water by making use of the high thermal deformation temperature which is 20 to 40° C. higher than that of the shaped articles of vinyl chloride resin compositions.

In the case of shaping, chlorinated vinyl chloride resins have a drawback that they have inferior thermal stability to vinyl chloride resin compositions, and thus they tend to be burnt in a shaping process. For example, a chlorinated vinyl chloride resin is colored when it is extrusion molded to produce a pipe for hot water, or in some cases, it is burnt during extrusion molding. Thus, such a produced pipe may not be commercially sold.

SUMMARY OF THE INVENTION

One object of the present invention is to provide a chlorinated vinyl chloride resin composition having good thermal stability, in particular, for the production of pipes.

Accordingly, the present invention provides a chlorinated vinyl chloride resin composition comprising a chlorinated vinyl chloride resin which has a polymerization degree of from 600 to 1500 prior to chlorination and a chlorination degree of from 62 to 70 wt. %, an impact modifier, a stabilizer, a lubricant and titanium dioxide, wherein the content of zinc in titanium dioxide is 0.1% or less.

DETAILED DESCRIPTION OF THE INVENTION

A vinyl chloride resin (prior to post-chlorination), which is a raw material of a chlorinated vinyl chloride resin contained in the composition of the present invention, has a polymerization degree of from 600 to 1500, preferably from 600 to 1300, more preferably from 600 to 1200. The chlorination degree of the chlorinated vinyl chloride resin is from 62 to 70 wt. %, preferably from 63 to 70 wt. %, more preferably from 65 to 70 wt. %.

When the polymerization degree of a vinyl chloride resin as the raw material of a chlorinated vinyl chloride resin is less than 600, sufficient mechanical strength cannot be attained. When this polymerization degree exceeds 1500, the processing of the resin composition is not easy.

When the chlorination degree of a chlorinated vinyl chloride resin is less than 62 wt. %, a resin composition does not have sufficient heat resistance. When the chlorination degree exceeds 70 wt. %, the resin has a high melt viscosity, and thus the processing of a resin composition undesirably encounters technical problems.

Herein, "vinyl chloride resins" include vinyl chloride homopolymers, and also copolymers of vinyl chloride with other copolymerizable monomer (e.g. ethylene, propylene, vinyl acetate, allyl chloride, allyl glycidyl ether, acrylate esters, vinyl ethers, etc.).

The composition of the present invention is characterized in the use of titanium dioxide containing 0.1% or less of zinc. The use of such titanium dioxide containing the small amount of zinc significantly improves the thermal stability of a resin composition.

Titanium dioxide having such a low zinc content can be produced by a chlorine method, while titanium dioxide is usually produced by a sulfuric acid method. Titanium dioxide having such a low zinc content is commercially available.

The amount of titanium dioxide is preferably at least 1 wt. parts, more preferably at least 2 wt. parts, per 100 wt. parts of the chlorinated vinyl chloride resin. When the amount of titanium dioxide is less than 1 wt. parts, the inherent whitening effect of zinc dioxide deteriorates, and obtained shaped articles, in particular, pipes have decreased impact strength.

The upper limit of the amount of titanium dioxide is not critical. Practically, the amount of titanium dioxide does not exceed 10 wt. parts per 100 wt. parts of the chlorinated vinyl chloride resin.

It is preferable for the chlorinated vinyl chloride resin composition of the present invention to contain an impact modifier, a stabilizer, a lubricant, etc. in addition to titanium dioxide so that the composition has well balanced impact resistance and heat resistance by taking processability into account.

An impact modifier may be any of conventionally used impact modifiers for chlorinated vinyl chloride resins, for example, those comprising MBS, ABS, MABS, chlorinated polyethylene (CPE), acrylic rubber, etc.

In particular, MBS or the combination of MBS and chlorinated polyethylene is preferably used as an impact modifier to balance the impact resistance and heat resistance. For the same reason, the amount of an impact modifier or impact modifiers is preferably between 4 and 15 wt. parts, more preferably between 4 and 12 wt. parts, per 100 wt. parts of a chlorinated vinyl chloride resin.

Stabilizers may be any conventional stabilizers for chlorinated vinyl chloride resins such as tin-base stabilizers, lead-base stabilizers, etc. Among them, tin-base stabilizers are preferable. Titanium dioxide containing such a small amount of zinc can most effectively display its effect to improve the thermal stability, when a tin-base stabilizer is used as a stabilizer.

Preferable examples of tin-base stabilizers are alkyltin compounds (e.g. methyltin, butyltin, octyltin, mixed metal alkyltin, etc.). Other examples of tin-base stabilizers are mercaptomethyltin, mercaptooctyltin, mercaptobutyltin, dialkyltinbis (alkylmercaptocarboxylate salt), octyltinmaleate, butyltin maleate, octyltin laurate, butyltin laurate, butyltin lauratemaleate, octyltin carboxylate, butyltin carboxylate, etc.

The amount of a stabilizer is preferably from 1.5 to 5 wt. parts, more preferably from 1.5 to 4 wt. parts, per 100 wt. parts of a chlorinated vinyl chloride resin. When the amount of a stabilizer is less than 1.5 wt. parts, the thermal stability of a chlorinated vinyl chloride resin composition deteriorates. When the amount of the stabilizer exceeds 5 wt. parts, the effect to improve the thermal stability reaches the limit, and thus the thermal stability is not improved in a degree comparable to the added amount of the stabilizer.

Examples of lubricants are polyglycerol of di- or trioleate, polyethylene, oxidized polyethylene, high molecular weight paraffin waxes, etc. Among them, polyethylene waxes are preferable.

The amount of a lubricant is preferably from 1.5 to 4 wt. parts, more preferably from 1.5 to 3 wt. parts, per 100 wt. parts of a chlorinated vinyl chloride resin. When the amount of a lubricant is less than 1.5 wt. parts, the composition has a high melt viscosity, and thus its extrusion precessability deteriorates. When the amount of a lubricant exceeds 4 wt. parts, the lubricity of the resin against metals becomes too high, and thus the composition may pulsate when it is discharged in the extrusion processing process.

The chlorinated vinyl chloride resin composition of the present invention may optionally contain other additives, which are compounded in conventional chlorinated vinyl chloride resin compositions, in addition to the above additives. Examples of the other additives are acrylic processing aids, colorants, and the like.

The chlorinated vinyl chloride resin composition of the present invention may be prepared by any conventional methods. For example, all the additives are added to the chlorinated vinyl chloride resin at a time and kneaded. Alternatively, the additives are added to the chlorinated vinyl chloride resin one after another and kneaded.

The kneading may be carried out with any conventional kneading machines.

EXAMPLES

The present invention will be explained in more detail by the following examples, which do not limit the scope of the invention in any way.

In the examples, "parts" and "%" are "wt. parts" and "wt. %", respectively, unless otherwise indicated.

Example 1

A vinyl chloride resin having a polymerization degree of 1,000 was post-chlorinated to obtain a chlorinated vinyl chloride resin having a chlorination degree of 67%.

MBS (Trade name "B561" manufactured by KANEKA CORPORATION) (6 parts) and a chlorinated polyethylene having a chlorination degree of 35% (Trade name "H135" manufactured by DAISO CO., LTD.) (3 parts) were added as impact modifiers to the above chlorinated vinyl chloride resin (100 parts) Furthermore, mercaptooctyltin (2 parts) as a stabilizer, two polyethylene waxes (Trade names "AC-617A" and "AC-629A" manufactured by Allied Signal) (each 1 part) as lubricants, and titanium dioxide having a zinc content of less than 0.01% (5 parts) as a filler were added. Then, the mixture was blended with a homogenizer at 10,000 rpm for 4 minutes, and a homogeneous composition was obtained.

The blend composition was subjected to a thermal stability test using a laboplastomill (manufactured by TOYO SEIKI) at 190° C. and 50 rpm with a loading amount of 65 g. A time, at which a torque started to increase after the rotation was started and then a torque became constant, was recorded as a decomposition-starting time. The decomposition-starting time of this composition was 13 minutes. The constant torque was 4.5 kg·cm.

Example 2

A chlorinated vinyl chloride resin composition was prepared in the same manner as in Example 1 except that 3 parts of titanium dioxide having a zinc content of less than 0.01% was added. Then, the obtained blend composition was subjected to the same thermal stability test as that in Example 1. The constant torque was 4.5 kg·cm, and the decomposition-starting time of this composition was 13 minutes.

Example 3

A chlorinated vinyl chloride resin composition was prepared in the same manner as in Example 1 except that 1 part of titanium dioxide having a zinc content of less than 0.01% was added. Then, the obtained blend composition was subjected to the same thermal stability test as that in Example 1. The constant torque was 4.5 kg·cm and the decomposition-starting time of this composition was 13 minutes.

Comparative Example 1

A chlorinated vinyl chloride resin composition was prepared in the same manner as in Example 1 except that 5 parts of titanium dioxide having a zinc content of 0.30% was added. Then, the obtained blend composition was subjected to the same thermal stability test as that in Example 1. The constant torque was 4.5 kg·cm, and the decomposition-starting time of this composition was 5.5 minutes.

Comparative Example 2

A chlorinated vinyl chloride resin composition was prepared in the same manner as in Example 1 except that 3 parts of titanium dioxide having a zinc content of 0.30% was added. Then, the obtained blend composition was subjected to the same thermal stability test as that in Example 1. The constant torque was 4.5 kg·cm, and the decomposition-starting time of this composition was 6.0 minutes.

Comparative Example 3

A chlorinated vinyl chloride resin composition was prepared in the same manner as in Example 1 except that 1 part of titanium dioxide having a zinc content of 0.30% was added. Then, the obtained blend composition was subjected to the same thermal stability test as that in Example 1. The constant torque was 4.5 kg·cm and the decomposition-starting time of this composition was 7.0 minutes.

Example 4

A vinyl chloride resin having a polymerization degree of 1,000 was post-chlorinated to obtain a chlorinated vinyl chloride resin having a chlorination degree of 67%.

MBS (Trade name "B561" manufactured by KANEKA CORPORATION) (6 parts), and a chlorinated polyethylene having a chlorination degree of 35% (Trade name "H135" manufactured by DAISO CO., LTD.) (3 parts) were added as impact modifiers to the above chlorinated vinyl chloride resin (100 parts). Furthermore, mercaptooctyltin (2 parts) as a stabilizer, two polyethylene waxes (Trade names "AC-617A" and "AC-629A" manufactured by Allied Signal) (each 1 part) as lubricants, and titanium dioxide having a zinc content of less than 0.01% (5 parts) as a filler were added. Then, the mixture was blended with a 300 liter super mixer while the temperature rose to 130° C., and a homogeneous composition was obtained.

The composition was extruded with a TEC conical extruder (manufactured by Toshiba) in the form of a pipe. In the extrusion, a resin temperature at the die tip was 194.6° C.

The Charpy impact strength of this pipe was measured at 23° C. and 0° C. according to JIS K-7111. The impact strength was 31 kg·cm/cm$^2$ at 23° C., and 21 kg·cm/cm$^2$ at 0° C.

A Vicat softening point was measured under a load of 5 kg according to JIS K-7206. The softening point was 113.4° C.

The color tone of the pipe had no redness (AA) by the visual inspection. Thus, the pipe was regarded as having good thermal stability.

Example 5

A chlorinated vinyl chloride resin composition was prepared in the same manner as in Example 4 except that 1 part of titanium dioxide having a zinc content of less than 0.01% was added, and then extruded in the form of a pipe by the same method as in Example 4. A resin temperature at the die tip was 194.6° C.

The Charpy impact strength of this pipe measured according to JIS K-7111 was 30 kg·cm/cm$^2$ at 23° C., and 20 kg·cm/cm$^2$ at 0° C.

The Vicat softening point of this pipe measured under a load of 5 kg according to JIS K-7206 was 113.4° C.

The color tone of the pipe had little redness (A) by the visual inspection. Thus, the pipe was regarded as having good thermal stability.

Example 6

A chlorinated vinyl chloride resin composition was prepared in the same manner as in Example 4 except that 8 parts of MBS (Trade name "B22" manufactured by KANEKA CORPORATION) was added as an impact modifier, and the amount of the lubricant AC-617A was changed to 1.3 parts, and then extruded in the form of a pipe by the same method as in Example 4. A resin temperature at the die tip was 193.6° C.

The Charpy impact strength of this pipe measured according to JIS K-7111 was 32 kg·cm/cm$^2$ at 23° C., and 22 kg·cm/cm$^2$ at 0° C.

The Vicat softening point of this pipe measured under a load of 5 kg according to JIS K-7206 was 114.3° C.

The color tone of the pipe had no redness (AA) by the visual inspection. Thus, the pipe was regarded as having good thermal stability.

Comparative Example 4

A chlorinated vinyl chloride resin composition was prepared in the same manner as in Example 4 except that 5 parts of titanium dioxide having a zinc content of 0.30% was added, and then extruded in the form of a pipe by the same method as in Example 4. A resin temperature at the die tip was 194.6° C.

The Charpy impact strength of this pipe measured according to JIS K-7111 was 31 kg·cm/cm$^2$ at 23° C., and 21 kg·cm/cm$^2$ at 0° C.

The Vicat softening point of this pipe measured under a load of 5 kg according to JIS K-7206 was 113.4° C.

The color tone of the pipe had redness (B) by the visual inspection. Thus, the pipe was regarded as having low thermal stability.

The above results are summarized in Tables 1 and 2.

TABLE 1

|  |  | Ex. 1 | Ex. 2 | Ex. 3 | C.E. 1 | C.E. 2 | C.E 3 |
|---|---|---|---|---|---|---|---|
| Chlorinated vinyl chloride resin |  | 100 | 100 | 100 | 100 | 100 | 100 |
| Impact modifier | MBS | 6 | 6 | 6 | 6 | 6 | 6 |
|  | CPE | 3 | 3 | 3 | 3 | 3 | 3 |
| Stabilzer: Mercaptooctyltin |  | 2 | 2 | 2 | 2 | 2 | 2 |
| Lubricant: Polyethylene waxes |  | 2 | 2 | 2 | 2 | 2 | 2 |
| Filler: TiO$_2$ | Zinc: 0.3% |  |  |  | 5 | 3 | 1 |
|  | Zinc: <0.01% | 5 | 3 | 1 |  |  |  |
| Plastomill properties |  |  |  |  |  |  |  |
| Thermal stability (min.) |  | 13 | 13 | 13 | 5.5 | 6 | 7 |
| Processability (constant torque) (kg · cm) |  | 4.5 | 4.5 | 4.5 | 4.5 | 4.5 | 4.5 |

TABLE 2

|  |  | Ex. 4 | Ex. 5 | Ex. 6 | C.E. 4 |
|---|---|---|---|---|---|
| Chlorinated vinyl chloride resin |  | 100 | 100 | 100 | 100 |
| Impact modifier | MBS(B561) | 6 | 6 |  | 6 |
|  | MBS(B22) |  |  | 8 |  |
|  | CPE | 3 | 3 |  | 3 |
| Stabilizer: Mercaptooctyltin |  | 2 | 2 | 2 | 2 |
| Lubricant: Polyethylene waxes |  | 2 | 2 | 2.3 | 2 |
| Filler: TiO$_2$ | Zinc: 0.3% |  |  |  | 5 |
|  | Zinc: <0.01% | 5 | 1 | 5 |  |
| Properties of pipe |  |  |  |  |  |
| Charpy impact strength(kg · m/cm$^2$) | at 23° C. | 31 | 30 | 32 | 31 |
|  | at 0° C. | 21 | 20 | 22 | 21 |
| Vicat softening point (° C.) (5 kg) |  | 113.4 | 113.4 | 114.3 | 113.4 |
| Color tone |  | AA | A | AA | B |

What is claimed is:

1. A chlorinated vinyl chloride resin composition comprising a chlorinated vinyl chloride resin which has a polymerization degree of from 600 to 1500 prior to chlorination and a chlorination degree of from 62 to 70 wt. %, an impact modifier, a stabilizer, a lubricant and titanium dioxide, wherein the content of zinc in titanium dioxide is less than 0.01%.

2. A chlorinated vinyl chloride resin composition according to claim 1, wherein said stabilizer is at least one tin-base stabilizer.

3. A chlorinated vinyl chloride resin composition according to claim 1, wherein an amount of said titanium dioxide is at least 1 wt. parts per 100 wt. parts of said chlorinated vinyl chloride resin.

4. A chlorinated vinyl chloride resin composition according to claim 1, wherein said impact modifier is MBS or a mixture of MBS and chlorinated polyethylene.

5. A chlorinated vinyl chloride resin composition according to claim 1, wherein an amount of said impact modifier is from 4 to 15 wt. parts per 100 wt. part of said chlorinated chloride resin.

6. A pipe made from a chlorinated vinyl chloride resin composition according to claim 1.

* * * * *

UNITED STATES PATENT AND TRADEMARK OFFICE
CERTIFICATE OF CORRECTION

PATENT NO.   : 6,306,950 B1
DATED        : October 23, 2001
INVENTOR(S)  : Toshio Okuhara et al.

It is certified that error appears in the above-identified patent and that said Letters Patent is hereby corrected as shown below:

<u>Title page,</u>
Item [30], Foreign Application Priority Data, please change the Priority Document number from "9-332894" to -- 9-332824 --.

Signed and Sealed this

Eighth Day of October, 2002

*Attest:*

JAMES E. ROGAN
*Attesting Officer*   *Director of the United States Patent and Trademark Office*